United States Patent
Dobbs et al.

[11] Patent Number: 5,444,752
[45] Date of Patent: Aug. 22, 1995

[54] TOMOGRAPHY DETECTOR TEMPERATURE EQUALIZATION

[75] Inventors: John Dobbs, Hamilton; David Banks, Boxford; Leonhard Katz, Winchester, all of Mass.

[73] Assignee: Analogic Corporation, Peabody, Mass.

[21] Appl. No.: 191,426

[22] Filed: Feb. 3, 1994

[51] Int. Cl.⁶ .............................. G01T 1/24
[52] U.S. Cl. ........................... 378/19; 378/4; 378/199
[58] Field of Search ............ 378/4, 19, 199, 200; 250/370.15

[56] References Cited

U.S. PATENT DOCUMENTS

| | | | |
|---|---|---|---|
| 4,338,521 | 7/1982 | Shaw et al. | 250/367 X |
| 4,456,826 | 6/1984 | Forster | 378/19 X |
| 4,651,338 | 3/1987 | Hahn | 378/199 |
| 4,709,559 | 12/1987 | Dotzauer et al. | 378/200 X |
| 4,831,639 | 5/1989 | Harte | 378/19 |
| 4,934,823 | 6/1990 | Strauss | 378/19 X |
| 4,969,167 | 11/1990 | Zupancic et al. | |

Primary Examiner—David P. Porta
Attorney, Agent, or Firm—Lappin & Kusmer

[57] ABSTRACT

Temperature control of solid state detectors carried on the rotating gantry of computed tomography equipment is impractical for very detailed images. The temperatures of all of the detectors in the array can be equalized, however, by closely coupling them to a thermally massive object and isolating this combination from the environment. Significant thermal gradients are thereby removed from the array, and time is removed as a calibrating factor. The detectors are mounted on a common heat sink which provides the thermal mass, and the heat sink is covered with insulation and attached to the gantry by thermally isolating mounts, such as thin flexible stainless steel plates.

17 Claims, 4 Drawing Sheets

TOMOGRAPHY DETECTOR TEMPERATURE EQUALIZATION

This application is related to co-pending U.S. patent application Ser. No. 08/19,945. filed in the name of John Dobbs and David Banks contemporaneously herewith and assigned to the present assignee (Attorney's Docket Number ANA-23); and U.S. patent application Ser. No. 08/191,428, filed in the name of Bernard M. Gordon; John Dobbs and David Banks contemporaneously herewith and assigned to the present assignee (Attorney's Docket Number ANA-44).

FIELD OF THE INVENTION

This invention relates generally to computer assisted tomography, and more particularly to the elimination of image artifacts caused by temperature drift in CAT scanner detector arrays.

BACKGROUND OF THE INVENTION

Computer assisted tomography, commonly called CAT or CT scanning, is a method of producing a density image of a cross section of a scanned object, usually a cross section of a human patient. In a CAT scanner of the third generation type, an x-ray source and an array of x-ray detectors are rotated in a scanning plane about a central area in which is located the patient object. X-rays from the source pass from a source point, commonly referred to as the focal spot, through the object and are received by individual detectors. The detectors are arranged in a single row in the shape of an arc of a circle having a center of curvature coincident with the focal spot of the x-ray source. Each detector, therefore, subtends an equal angle relative to the focal spot so that all of the detectors are each theoretically subjected to the sane x-ray exposure levels from an tinattenuated beam during an intensity measurement.

The x-rays that are detected by a single detector at a measuring instant during a scan is considered a "ray." The ray is partially attenuated by all the mass in its path so as to generate a single intensity measurement as a function of the attenuation, and thus the density of the mass in that path. A projection or view, i.e., the x-ray intensity measurement, is typically done at each of a plurality of angular positions for a given position of the disk.

An image reconstructed from data acquired at all of the projection angles during the scan will be a cross-sectional slice in the scanning plane through the object being scanned. In order to "reconstruct" a density image of the cross-section of the object, the image is typically "back projected" using a mathematical algorithm attributed to Radon. Back projection usually involves the reconstruction of the image in a pixel array, wherein each pixel in the array is attributed to a value representative of the density of that volume of the patient which has the area of the pixel and the height equal to the slice thickness. As the source and detectors rotate around the object, rays penetrate the object from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the slice plane.

Because of the operation of the Radon algorithm, however, inconsistencies in the exposure measurements by any detectors result in artifacts such as extraneous rings appearing in the image. One cause of such inconsistencies is relative motion between source, object and detectors. Contributions to this cause are addressed, for example, in co-pending applications U.S. Ser. No. 08/190,945, filed Feb. 3,1994, in the names of John Dobbs and David Banks and entitled "Modular Detector Arrangement for X-ray Tomographic Detector System" (Attorney's Docket No. ANA-23); and U.S. Ser. No. 08/191,428, filed Feb. 3, 1994, in the names of Bernard M. Gordon, John Dobbs and David Banks and entitled "X-ray Tomography System for and Method of Improving the Quality of a Scanned Image" (Attorney's Docket No. ANA-44), both being assigned to the present assignee and both being filed simultaneously with this application.

Another cause of inconsistency in the exposure measurements by any of the detectors that tends to obscure image detail is an uncompensated change in detector sensitivity of one or more detectors relative to the other detectors. The combination of a rapid scan to minimize patient object motion, and the need to differentiate among soft tissues results in the use of and the need to detect very low levels of x-radiation. The most sensitive and therefore potentially useful detectors for this application are solidstate devices made up of a cadmium tungstate scintillating crystal for converting the x-ray energy to light and a semiconductor photo-diode to convert the light to an electrical signal that can be computer processed. Unfortunately, however, both of these devices are very temperature sensitive, and operation of the x-ray source and power supplies generates a large amount of heat that causes the ambient temperature to rise significantly. Furthermore, while the photo-diodes tend to consistently have a similar temperature coefficient, the cadmium tungstate crystals do not. In fact, even the sign of the coefficient may vary from crystal to crystal. A miscalibration of as little as 0.1%, however, can result in visible rings in the reconstructed image. Accurate temperature control or compensation for each of the solid state detectors is therefore an important requirement.

Adequate temperature control of all of the detectors, however, is far from easy. The ultimate solution would seem to be to measure the temperature of each detector and control it with a servo loop. However, with several hundred detectors mounted closely together in an array, and each detector being less than two millimeters in width, such an approach is impractical. Yet, even simple temperature control of the detector array as a single entity presents many problems. Mounting an air conditioning system on the rotating gantry takes up a great deal of scarce space and hinders accessibility to other components. U.S. Pat. No. 4,969,167 that issued to Zupancic et. al. on Nov. 6, 1990, describes a system that supplies ambient air at elevated pressure in the vicinity of the detectors to cool them. While this may indeed reduce the range of inconsistencies among detectors, it does not allow accurate calibration to within 0.1%.

The current invention is driven by the recognition that any practical type of temperature control of the detector array, in which heat is added to or subtracted from the array, will cause thermal gradients within the array. In order to accurately calibrate a detector array with thermal gradients, however, one must duplicate not only the heat sources to which the array is exposed during a scanning operation, but the time delays as well. But in typical operation, CAT scanners experience very non-uniform time schedules based on individual patient needs, duplicate scans required because of inadvertent patient motion, and non-uniform work load. Conversely, to limit the equipment to a rigid time schedule to duplicate calibration conditions would be unrealistic. Because of the seriousness of these problems several CT equipment makers have abandoned the use of these efficient solid state detectors in their latest designs.

If, on the other hand, thermal gradients within the detector array could be eliminated, all of the detectors would operate substantially at a common measurable temperature, and time would not be a factor. A single temperature measurement would accurately reflect the temperature of each detector, making individual temperature compensation for each measurement a simple matter. That is substantially what is accomplished by this invention.

OBJECTS OF THE INVENTION

It is a general object of the invention to substantially eliminate thermal gradients across the detector array during operation of the a CT scan machine so that the detectors operate at substantially the same temperature.

It is another object of the present invention to equalize the temperature of the detectors of an array of a CT scanner so that the temperature of the detectors can be easily measured and compensation provided for each detector based upon predetermined measurements.

Yet another object of the present invention is to substantially raise the thermal mass of the support assembly for supporting the detector array (preferably by several orders of magnitude) so that heat that reaches the detectors from the environment will not change the temperature of the detectors appreciably.

Still another object of the present invention is to lower the rate of heat conduction between the detector assembly and the environment so that little heat conduction occurs between the assembly and the enviromnent.

Other objects of the invention will in pan be evident and will in part appear hereinafter. The invention accordingly comprises the apparatus possessing the construction, combination of elements, and arrangement of pans which are exemplified in the following detailed disclosure, and the scope of the application of which will be indicated in the claims.

SUMMARY OF THE INVENTION

In addition to temperature control apparatus that transfers heat to the detector array carried on a rotating gantry disk of computed tomography equipment, the temperature equalizing apparatus of the invention comprises heat sink means for supporting the detector array, the heat sink means having high thermal conductance for closely interconnecting all of the detectors thermally, and thermal isolating means for minimizing heat transfer to and from the combination of heat sink and detector array. In general, the detector array is secured to a heat sink which includes a substantially large thermal mass (by approximately two or more orders of magnitude larger than the detector array) so as to reduce the effect of a given amount of heat within the detector array assembly and slow down variations of temperature with time. Further, the detectors of the detector array are coupled to the heat sink, and the heat sink and detectors are substantially thermally isolated from the outside environment.

BRIEF DESCRIPTION OF THE DRAWINGS

For a fuller understanding of the nature and objects of the present invention, reference should be made to the following detailed description taken in connection with the accompanying drawings wherein.

DETAILED DESCRIPTION OF THE DRAWINGS

Figure 1:
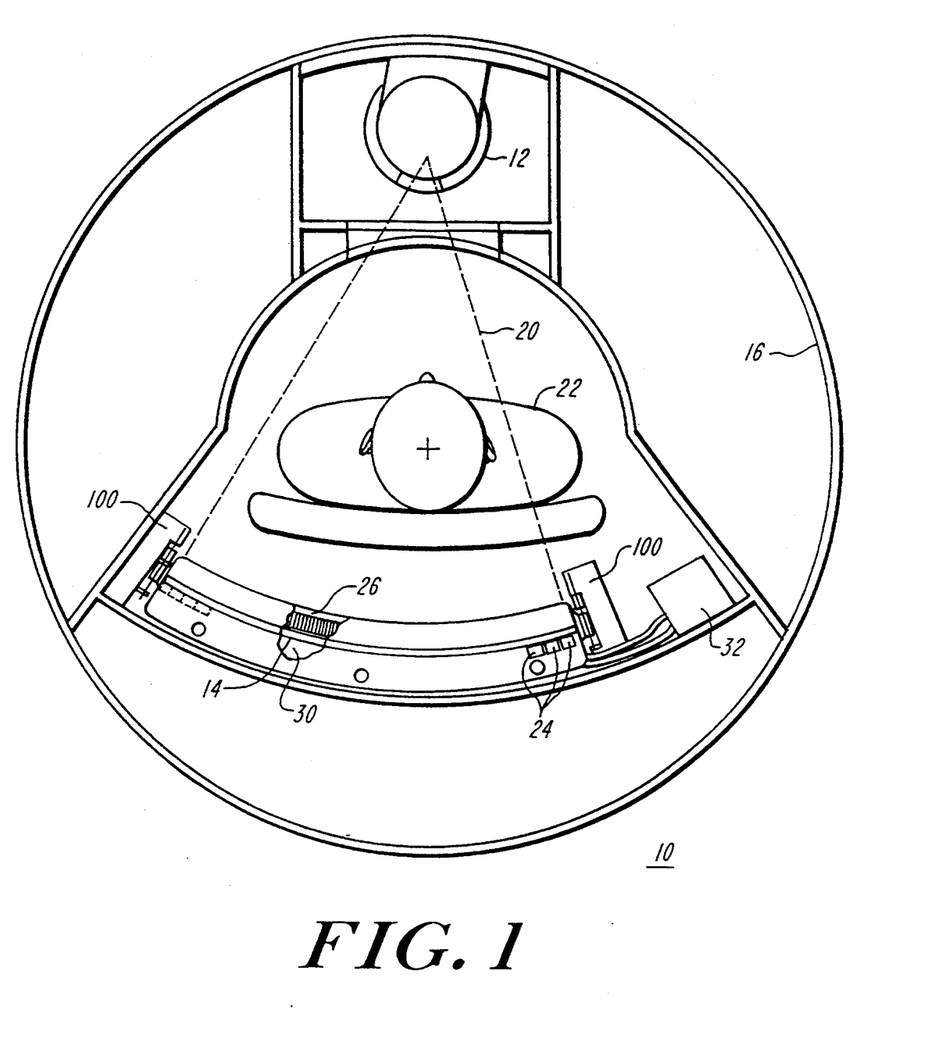
FIG. 1 is an end view of part of a CAT scanner embodying the invention.

For a more complete understanding of the invention, refer now to FIG. 1, which represents a portion of a computed tomography (CAT) scanner 10 that embodies the detector temperature equalizing apparatus of the invention. In scanner 10, a source of x-rays 12 and an array of x-ray detectors 14 are carried on opposite sides of a rotating gantry 16, adapted to rotation about the center of rotation 18. The disk includes an aperture 20 for receiving the patient object 22 so that it is positioned between source 12 and detectors 14 as the source and detectors rotate about the rotation center 18 during a scan. Detectors 14 measure the intensity of x-rays provided from source 12 through aperture 20, and provide electrical output to a computer over multi-conductor cables 24, a separate conductor lead being provided from each individual detector. Anti-scatter plates 26 between detectors 14 and object 22 eliminate scattered x-rays, i.e., those which do not come in a straight line from source 12. In this example there may be 384 detectors and corresponding sets of anti-scatter plates and leads extending uniformly over an arc of 48 degrees having a center of curvature coincident with the focal spot of source 12. Detectors 14 are attached to a spine 30, both of which, according to the invention may be covered by a cover 70 as described in greater detail hereinafter. Each end of spine 30 is attached to gantry disk 16 by a support 100 described hereinafter. A circulating pump 32 circulates a heat transfer fluid through spine 30.

Figure 2:
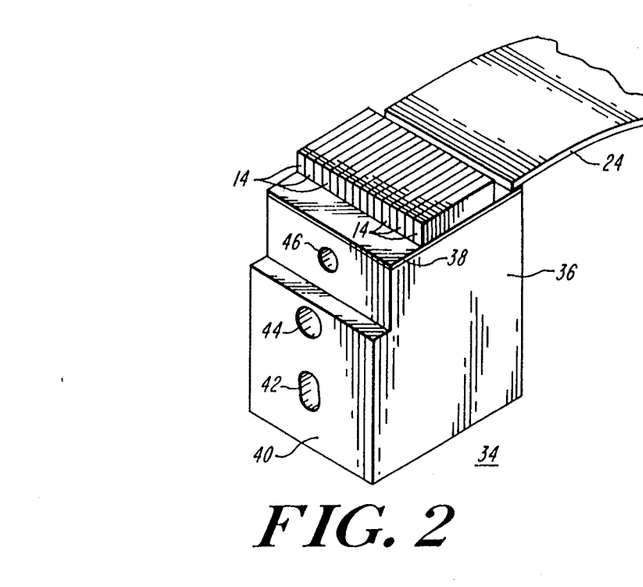
FIG. 2 is an isometric view of a detector module useful in the embodiment of FIG. 1.
Figure 3:
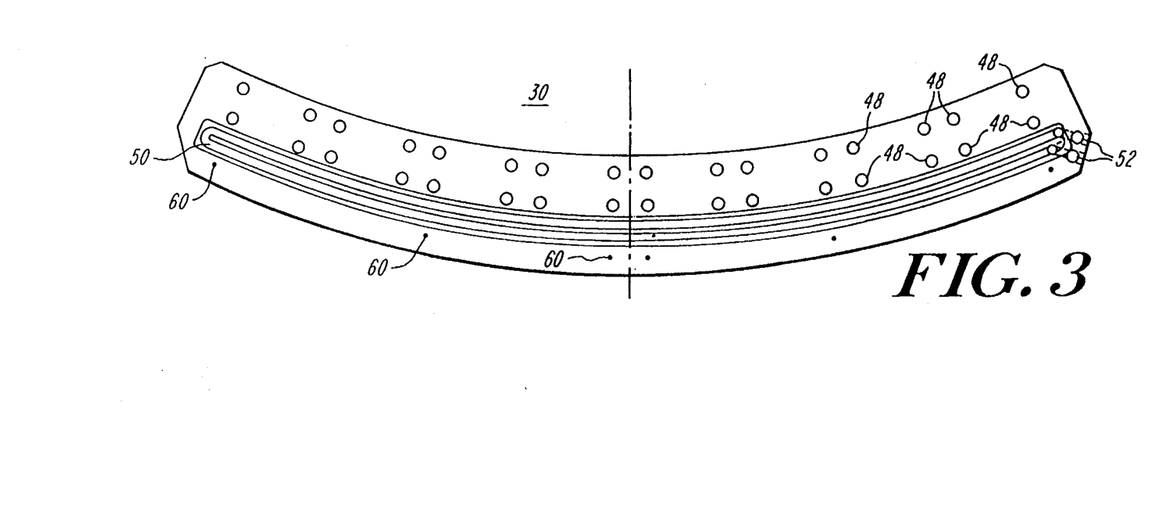
FIG. 3 is a back elevation of a spine useful in the embodiment of FIG. 1.
Figure 4:
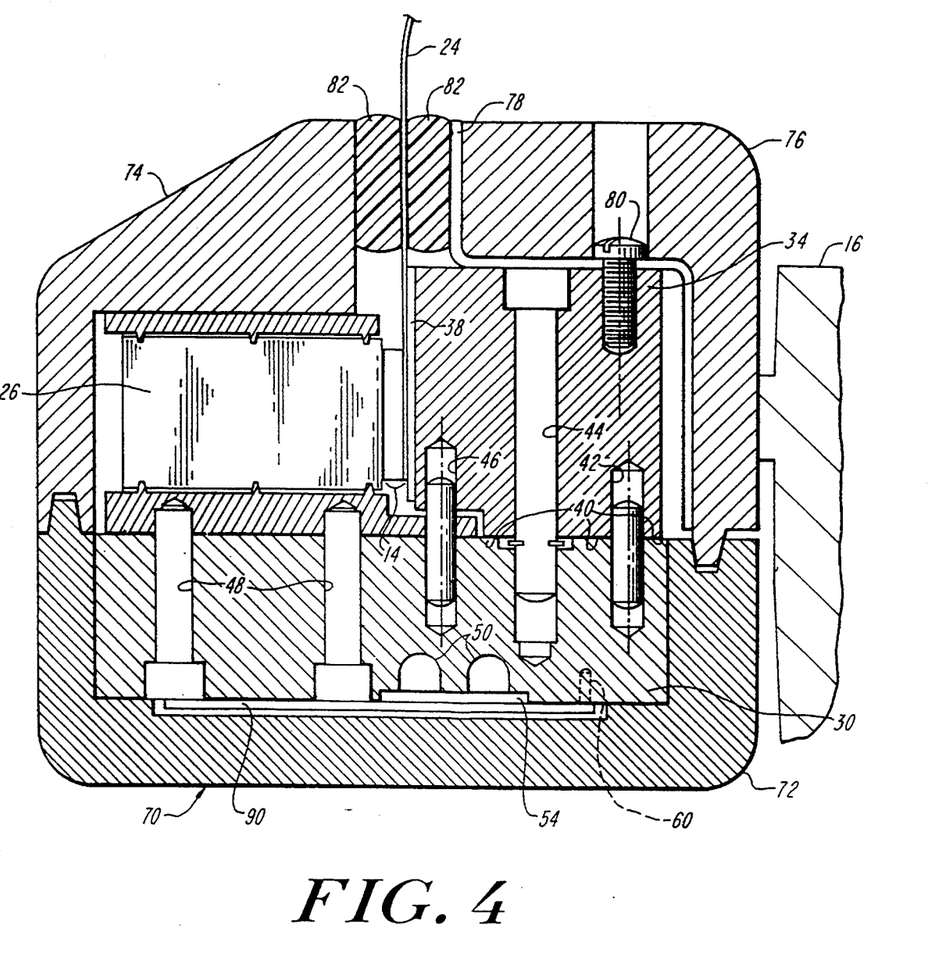
FIG. 4 is a cross sectioned view of the assembly of spine, modules and cover of FIG. 1.

FIGS. 2, 3 and 4 show in detail one arrangement for mounting the detectors according to the invention. In the construction shown in FIG. 2, a plurality of detectors 14, e.g. sixteen detectors, are assembled into a module 34. Although not shown, each detector 14 comprises a scintillating crystal disposed on a semiconductor diode. The latter, in turn, is supported on a substrate 38, the back side of which is attached to a solid block 36 preferably made of a material with high thermal conductivity such as, for example, aluminum. Sixteen matching crystals are attached so as to illuminate the respective diodes. Both attachments may be by a thin layer of epoxy or other cement. Multi-conductor cable 24 may be soldered to the diode output leads on substrate 38 so as to provide an electrical output from each detector to a computer (not shown) for data storage and image generation. Block 36 has a large, flat surface 40 for excellent thermal contact with spine 30, and may have a pair of locating holes 42 and 44 and a bolt hole 46 for attachment to spine 30. The features of this modular arrangement which lead to accurate placement and alignment of the detectors and anti-scatter plates are discussed in detail in the previously mentioned concurrently filed application "Modular Detector Arrangement for X-ray Tomographic Detector System." What is important for this application is the very high thermal conductivity among and between detectors 14 and spine 30.

In accordance with the present invention, the spine 30 forms a heat sink of a substantially large thermal mass (preferably by approximately two or more orders of magnitude larger than the typical support in the form of a printed circuit board used in certain prior art systems, and preferably approximately two or more orders of magnitude larger than the detector array itself) so as to reduce the effect of a given amount of heat within and slow down variations of temperature with time. Further, the detectors of the detector array are coupled to the heat sink, and the heat sink and detectors are substantially thermally isolated from the outside environment.

FIG. 3 shows a view of the back surface of spine 30 opposite to the front surface upon which modules 34 are attached. In addition to thirty-two through holes, some of which are indicated at 48 in FIG. 3, for the attachment of eight anti-scatter modules, each containing forty-eight anti-scatter plates 26, spine 30 is provided with a passage 50 for the circulating of a heat transfer fluid, such as water. The fluid, pumped by circulating pump 32 shown in FIG. 1, is transferred to passage 50 through a pair of holes 52 provided in the spine. Passage 50 may be covered by a simple flat cover 54 which is shown in the cross-section drawing of FIG. 4. Cover 54 may be cemented to spine 30 with a gasket-forming material such as, for example, RTV. Similar to block 36 of detector module 34, in accordance with the invention spine 30 is made of a material of high thermal conductivity. Aluminum, being strong and inexpensive, is one obvious, but not exclusive choice. Other materials known for their high thermal conductivity, which may contain for example, silver, copper, magnesium and the like, would obviously suffice for both spine 30 and block 36 of detector module 34. While the circulation of heat transfer fluid, and therefore passage 50 is not essential to the invention, it can improve the thermal conductivity throughout the length of the spine in order to more closely equalize the temperatures of all of the detectors according to the invention. Strategically, spaced small holes 60 along the backside of spine 30 may be used to receive temperature sensing elements such as thermocouples or diodes. While only one sensor is needed to determine the temperature of all the detectors for compensation purposes, the use of three or more allows verification that the entire spine is indeed operating at a uniform temperature within 0.1° C.

The assembly cross sectional view of FIG. 4 shows the large amount of flat surface area 40 of detector modules 34 in direct contact with spine 30 for very high thermal conductivity. It also shows the location of fluid circulating passage 50 in the vicinity of the detector modules for efficiency in equalizing the temperature along spine 30. With paths of such high thermal conductivity connecting all of the detectors, coupled with the fact that the detectors themselves do not generate a significant amount of heat, the only location in which calibration-disturbing thermal gradients can appear is through exchange of a significant amount of heat with the environment surrounding the array of detectors 14.

In order to protect the detector array from gain or loss of heat through convection or radiation, in accordance with the invention, a suitable cover 70 is provided, the details of which are shown in FIG. 4. Cover 70, for convenience, is made up of three parts; a back half section 72 secured directly to spine 30; a front inner quarter section 74 secured to the anti-scatter modules 34; and a plurality of front outer quarter sections 76 (only one being shown in FIG. 4, the others being distributed in the longitudinal direction of the spine, perpendicular to the plane of the figure shown in FIG. 4, to facilitate easy access to the detectors and anti-scatter plates) secured to a formed sheet 78 of firm metal or plastic. The sections can be secured by cementing the sections to the associated parts. Screws 80 through sheet 78 into detector modules 34 make section 76 removable for easy replacement of one or more detector modules. These three sections may have rounded edges to increase durability and reduce turbulence as the gantry disk rotates about the rotation center 18. They may be composed of firm insulating material of very low thermal conductivity, such as polystyrene foam. To keep convection currents from coming in contact with the spine or modules, inner and outer quarter sections 74 and 76, respectively, have a strip of pliable insulation 56 along one edge to form a gasket 82 around output cables 24. The use of an electrically conducting foam for gasket 82 is found to help protect the electronic components from electrostatic charges, which might otherwise build up on the nonconducting foam and discharge through cables 24. A similar soft gasket may surround the hoses that conduct the circulating fluid between pump 32 and passage 50, but it needn't be electrically conductive, Being opaque to infra red as well as visible radiation, (albeit not to x-rays), cover 70 substantially reduces heat transfer to or from the detector array by radiation; and being of very low thermal conductivity, and enclosing the array, it prevents significant conductive heat transfer between the array and its outer skin, where convection transfer could take place.

A wide, flat heating element 90, preferably attached along the length of the back of spine 30, is useful for calibrating the detectors. For calibration, electrical power may be applied to heater 90 so as to raise the spine temperature. Because of the uniform application of heat by heater 90 over practically the entire spine surface, and the high thermal conductivity between the spine surface and all of the detectors, equilibrium at uniform detector temperature can be reached quickly, i. e., within a few minutes, and verified by at least three temperature sensors in holes 60. Individual detector dark current readings at each calibrating temperature are easily obtained. Individual highscale readings at each calibrating temperature, obtained by operating the x-ray source with only air between the source and the detectors, enables the generation of a computer look-up table to provide the correct compensation factor for each detector. During normal CAT scan operation, in response to the sensed spine temperature, the proper compensation factor from the look-up table can be automatically applied to each respective detector output measurement for construction of the image.

Figure 5:
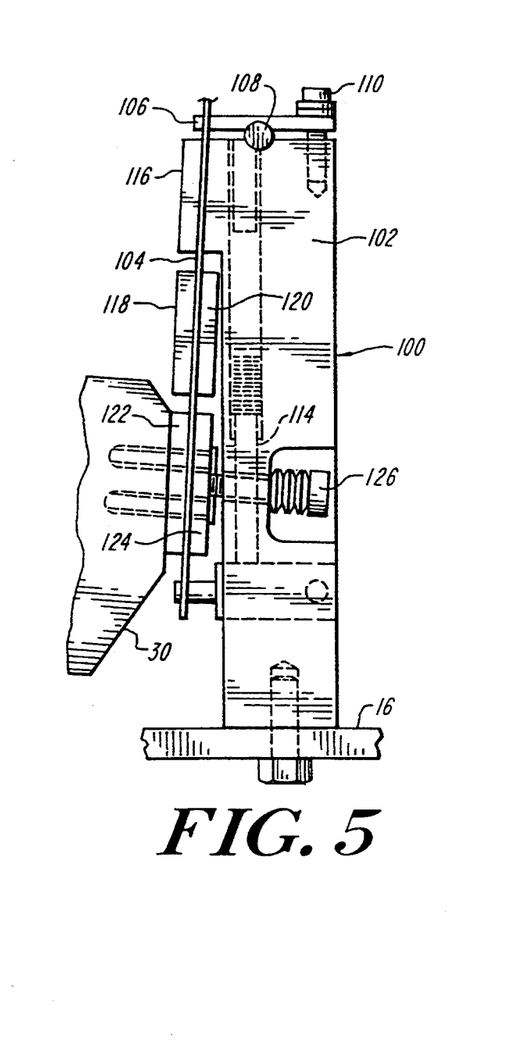
FIG. 5 is a front view, partially cut away, of an end support for supporting the spine and modules of FIG. 1.
Figure 6:
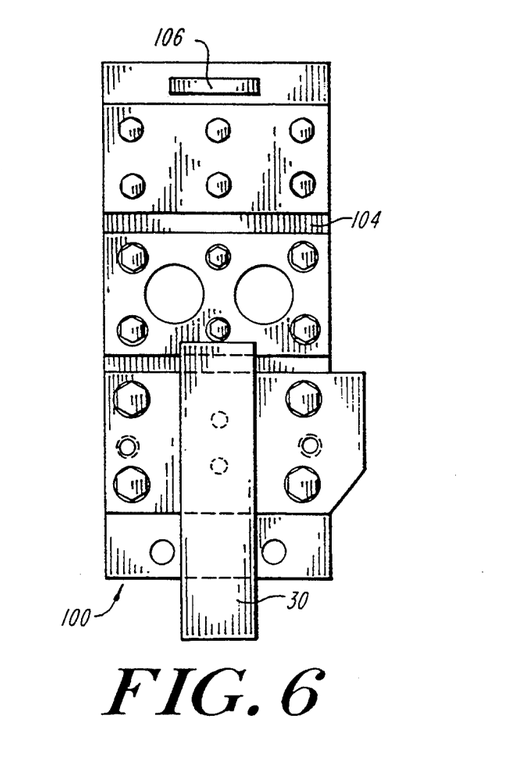
FIG. 6 is a cross-sectioned view of the end support shown in FIG. 5.
Figure 7:
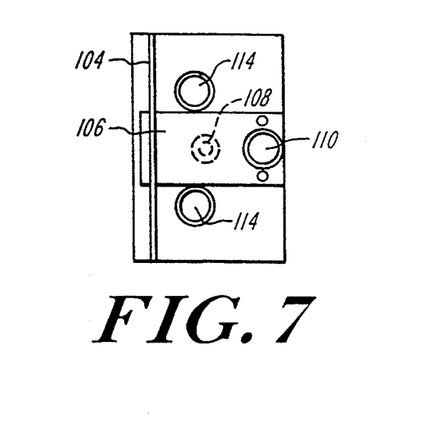
FIG. 7 is a top view of the end support shown if FIGS. 5 and 6.

Finally, the last remaining area for the possible transfer of sufficient heat to cause disturbing thermal gradients within the detector array lies in the attachment of the spine to the gantry. FIGS. 5–7 shows in three views, a support 100 for each end of spine 30 that reduces such heat transfer to a very low level. The major components of a support 100 with respect to this invention are a support body 102, which may be bolted to gantry disk 16, and a thin, flexible mounting plate 104, which may be bolted to body 102 and spine 30. Since virtually all conductive heat transfer between spine 30 and gantry disk 16 must pass through plate 104 and body 102, it is sufficient if either is of very low thermal conductivity. Thus, either or both can be made of a tough plastic or other similar material. In the preferred embodiment, however, plate 104 is made of stainless steel, which is strong and durable and has quite low thermal conductivity. Since plate 104 has a very thin cross-section, it provides sufficiently low thermal conduction to allow support body 102 to be of more convenient materials, including aluminum.

Supports 100 may advantageously have many features that are directed toward the accurate location of the detector array. A lever arm 106 that protrudes through a slot in the inner end of plate 104 and bears on a pivot ball 108 is driven by a screw 110 to finely adjust the distance between the detector array and the x-ray source. A pair of pivot arms 112 protrude through respective holes in the outer end of plate 104 and are driven by respective spring-loaded rods 114 to keep plate 104 under constant tension. A set of five stiffeners 116, 118, 120, 122, and 124 restrict the bending of plate 104 to two parallel areas. This restricts the tangential movement of the detector array to keep all detectors equidistant from the x-ray source. At one end of spine 30, a screw (not shown) through the center of body 102 bears against stiffener 124 to adjust the detector array tangentially, while a pair of spring loaded screws 126 through body 102 and into stiffener 124 eliminate backlash from the adjustment. These features are treated in greater detail in the aforementioned co-pending application "Modular Detector Arrangement for X-ray Tomographic Detector System" (Attorney's Docket No. ANA-23). In addition, in accordance with the principles of the present invention, the plates 122 and 124 are also made of low conductivity stainless steel so as to further thermally isolate the detectors of the detector array.

We have thus described apparatus that closely couples thermally all of the detectors within the array and isolates the array from its environment. Since there is no substantial heat source within the array, the result is substantial elimination of thermal gradients within the array. In response to the sensed array temperature, an accurate individual compensating factor (predetermined for that temperature) can be applied to each respective detector measurement. Solid state detectors can therefore be used at very low x-ray levels to provide high quality very detailed images of soft tissue.

While one embodiment of the invention has been described herein, it will be obvious that innumerable variations can be devised by others skilled in the art which, none the less do not depart from the spirit and scope of the invention, as define by the claims that follow.

What is claimed is:

1. Temperature equalizing apparatus for an array of detectors carried on a rotating gantry disk of computed tomography equipment, said apparatus comprising:
   heat sink means including a body having high thermal conductance and a thermal mass that is larger than a thermal mass of said array of detectors, said body being thermally coupled to said array of detectors for closely thermally interconnecting said detectors in said array; and
   thermal isolating means for minimizing heat transfer to and from said combination of heat sink means and detectors.

2. Temperature equalizing apparatus as in claim 1, wherein said thermal isolating means comprises:
   insulating cover means having low thermal conductance for enclosing said heat sink means and said detectors to substantially reduce heat transfer to and from said detectors by radiation and convection; and
   support means having low thermal conductance for mechanically attaching but thermally isolating said heat sink means and said rotating gantry.

3. Temperature equalizing apparatus as in claim 2, wherein said heat sink means comprises a rigid detector array support for mechanically supporting said detectors.

4. Temperature equalizing apparatus as in claim 3, wherein said heat sink means further comprises a plurality of module blocks attached to said detector array support, each of said module blocks having attached thereto a respective group of said detectors.

5. Temperature equalizing apparatus as in claim 4, wherein said module blocks are aluminum.

6. Temperature equalizing apparatus as in claim 4, wherein said detector array support further comprises a fluid conduit recessed into said detector array support opposite the attachment of said module blocks to further mi between detectors in said array.

7. Temperature equalizing apparatus as in claim 4, wherein said insulating cover means comprises rigid low density material substantially surrounding said detector array support.

8. Temperature equalizing apparatus as in claim 7, wherein said groups of detectors have attached thereto respective electrical output cables, and wherein
   said cover means further comprises resilient gasket means for bearing against said electrical output cables.

9. Temperature equalizing apparatus as in claim 8, wherein said electrical output cables are electrically insulated and said resilient gasket means is electrically conductive.

10. Temperature equalizing apparatus as in claim 7, wherein said cover means comprises a removable section attached to a plurality of said module blocks for providing access to said module blocks.

11. Temperature equalizing apparatus as in claim 3, wherein said detector array support is aluminum.

12. Temperature equalizing apparatus as in claim 3, wherein said detector array support further comprises fluid conduit means for circulating a heat transfer fluid along said detector array support to minimize temperature gradients within said spine.

13. Temperature equalizing apparatus as in claim 3, further comprising a plurality of temperature sensors for sensing the temperature of said detector array support at a plurality of locations.

14. Temperature equalizing apparatus as in claim 3, wherein said support means comprises:
   two supports, each attached to a respective end of said detector array support.

15. Temperature equalizing apparatus as in claim 14, wherein each of said supports comprises:
   a rigid support body attached to said gantry disk; and
   a thin, flexible plate attached to said detector array support end and to said support body.

16. Temperature equalizing apparatus as in claim 15, wherein the thickness of said flexible plate is small compared to its effective thermal path length between said detector array support and said support body.

17. Temperature equalizing apparatus as in claim 1, wherein said heat sink means includes a thermal mass larger by at least two orders of magnitude than the thermal mass of the detector array so as to thermally couple the detectors of the array together.

* * * * *

UNITED STATES PATENT AND TRADEMARK OFFICE
CERTIFICATE OF CORRECTION

PATENT NO. : 5,444,752
DATED : August 22, 1995
INVENTOR(S) : John Dobbs, David Banks, Leonhard Katz It is certified that error appears in the above-indentified patent and that said Letters Patent is hereby corrected as shown below:

Claim 6, column 8, line 39, delete "mi" and substitute therefor --minimize temperature differences--.

Signed and Sealed this

Ninth Day of January, 1996

Attest:

BRUCE LEHMAN

*Attesting Officer*      *Commissioner of Patents and Trademarks*